(12) United States Patent
Honma et al.

(10) Patent No.: US 7,411,092 B2
(45) Date of Patent: Aug. 12, 2008

(54) QUATERNARY AMMONIUM SALTS

(75) Inventors: Nobuaki Honma, Ibaraki (JP); Yoshimi Yamada, Osaka (JP)

(73) Assignee: Koei Chemical Company, Limited, Osaka-Shi (JP)

( * ) Notice: Subject to any disclaimer, the term of this patent is extended or adjusted under 35 U.S.C. 154(b) by 216 days.

(21) Appl. No.: 10/545,417

(22) PCT Filed: Feb. 6, 2004

(86) PCT No.: PCT/JP2004/001247

§ 371 (c)(1),
(2), (4) Date: Aug. 12, 2005

(87) PCT Pub. No.: WO2004/072015

PCT Pub. Date: Aug. 26, 2004

(65) Prior Publication Data
US 2006/0166103 A1    Jul. 27, 2006

(30) Foreign Application Priority Data

Feb. 13, 2003 (JP) ............................. 2003-035022
Feb. 14, 2003 (JP) ............................. 2003-036875

(51) Int. Cl.
*C07C 211/63* (2006.01)
(52) U.S. Cl. .................... 564/292; 564/293; 564/294
(58) Field of Classification Search ................. None
See application file for complete search history.

(56) References Cited

U.S. PATENT DOCUMENTS

2002/0015881 A1    2/2002    Nakamura et al.
2003/0013021 A1    1/2003    Wariishi

FOREIGN PATENT DOCUMENTS

JP    2001-35253 A    2/2001

OTHER PUBLICATIONS

Database CAPLUS on STN, Acc. No. 2001:933917, Nakamura et al., JP 2001-357896 (Dec. 26, 2001) (abstract).*
JP 2001-035253 A (Feb. 9, 2001) English machine translation.*

* cited by examiner

*Primary Examiner*—Brian J Davis
(74) *Attorney, Agent, or Firm*—Birch, Stewart, Kolasch & Birch, LLP

(57) ABSTRACT

A quaternary ammonium salt of the following formula (1):

$$\{(R^1)_a(R^2)_b(R^3)_c(R^4OCH_2CH_2OCH_2CH_2)_dN\}^+ \cdot A^- \quad (1)$$

[wherein, $R^1$, $R^2$ and $R^3$ may be mutually the same or different and represent an alkyl group having 1 to 4 carbon atoms or an alkyloxyethyl group of the formula (2):

$$R^5OCH_2CH_2— \quad (2)$$

(wherein, $R^5$ represents a methyl group or ethyl group), $R^4$ represents a methyl group or ethyl group, and any two of $R^1$, $R^2$ and $R^3$ may mutually bond at the end to form an alkylene chain, a, b and c represent an integer of 0 to 3, d represents an integer of 1 to 4, the sum of a, b and c is 3 or less, the sum of a, b, c and d is 4, and $A^-$ represents a bis(trifluoromethylsulfonyl)imidate ion $[N(SO_2CF_3)_2^-]$, tetrafluoroborate ion $(BF_4^-)$ or hexafluorophosphate ion $(PF_6^-)$].

6 Claims, No Drawings

QUATERNARY AMMONIUM SALTS

The present application is the 35 USC § 371 national phase of International Application No. PCT/JP2004/001247 filed on Feb. 6, 2004, which designated the United States of America, and claims priority thereto under the provisions of 35 USC § 120. The present application also claims priority under 35 USC § 119 to Japanese Applications 2003-035022 and 2003-036875, which were filed in the Japan Patent Office (JPO) on Feb. 13, 2003 and Feb. 14, 2003, repectively.

TECHINICAL FIELD

The present invention relates to a quaternary ammonium salt.

BACKGROUND TECHNOLOGY

A quaternary ammonium salt manifesting liquid condition at ordinary temperature (25° C.) is paid attention to as an organic synthesis reaction solvent (see, T. Welton, Chem. Rev., 99, 2071-2083 (1999)). As described in the above-mentioned literature, a quaternary ammonium salt such as an ethylmethylimidazolium salt and the like can be used as a reaction solvent capable of being utilized repeatedly and is paid attention to as a novel solvent giving low environmental load also from the standpoint of green chemistry, because of properties such as that the salt has extremely low volatility, is thermally stable and capable of standing a reaction at higher temperatures, that the salt is chemically stable, further that the salt shows high solubility for various organic compounds, and the like. Furthermore, application thereof as an electrolyte for organic electrolytic synthesis is expected, because of properties such as ion conductivity, electrochemical stability and the like. As the quaternary ammonium salts showing liquid condition at room temperature, for example, an N-butyl-N-methylpiperidinium salt, N-butyl-N-methylpyrrolidinium salt and the like are mentioned, and as the anion thereof, there are known a bis(trifluoromethylsulfonyl)imidate ion $[N(SO_2CF_3)_2^-]$, tetrafluoroborate ion $(BF_4^-)$, hexafluorophosphate ion $(PF_6^-)$ and the like.

In such applications, from the standpoint of promotion of the reaction by the means of stirring load or substance transfer, there has been a desire for development of a quaternary ammonium salt of lower viscosity.

DISCLOSURE OF THE INVENTION

The present invention provides a quaternary ammonium salt having lower viscosity as compared with the conventional quaternary ammonium salt being liquid at ordinary temperature (hereinafter, meaning 25° C.).

The present inventors have intensively studied to solve the above-mentioned problem, and resultantly found that a quaternary ammonium salt having at least one alkyloxyethoxyethyl group as a substituent has lower viscosity than the conventional quaternary ammonium salt.

Namely, the present invention provides the following [1] to [10].

[1] A quaternary ammonium salt of the following formula (1):

$$\{(R^1)_a(R^2)_b(R^3)_c(R^4OCH_2CH_2OCH_2CH_2)_dN\}^+ \cdot A^- \quad (1)$$

[wherein, $R^1$, $R^2$ and $R^3$ may be mutually the same or different and represent an alkyl group having 1 to 4 carbon atoms or an alkyloxyethyl group of the formula (2):

$$R^5OCH_2CH_2— \quad (2)$$

(wherein, $R^5$ represents a methyl group or ethyl group), $R^4$ represents a methyl group or ethyl group, and any two of $R^1$, $R^2$ and $R^3$ may mutually bond at the end to form an alkylene chain, a, b and c represent an integer of 0 to 3, d represents an integer of 1 to 4, the sum of a, b and c is 3 or less, the sum of a, b, c and d is 4, and $A^-$ represents a bis(trifluoromethylsulfonyl)imidate ion $[N(SO_2CF_3)_2^-]$, tetrafluoroborate ion $(BF_4^-)$ or hexafluorophosphate ion $(PF_6^-)$].

[2] The quaternary ammonium salt according to [1] wherein at least one of $R^1$, $R^2$ and $R^3$ represents a methyl group, and the sum of a, b and c is 1 to 3.

[3] The quaternary ammonium salt according to [1] wherein any two of $R^1$, $R^2$ and $R^3$ represent a methyl group, and the sum of a, b and c is 1 to 3.

[4] The quaternary ammonium salt according to [1] wherein the quaternary ammonium salt is represented by the following formula (3):

$$(R^6R^7R^8R^9N)^+ \cdot A^- \quad (3)$$

[wherein, $R^6$, $R^7$, $R^8$ and $R^9$ may be mutually the same or different and represent an alkyl group having 1 to 4 carbon atoms or an alkyloxyethoxyethyl group of the formula (4):

$$R^4OCH_2CH_2OCH_2CH_2— \quad (4)$$

(wherein, $R^4$ represents a methyl group or ethyl group), and any two of $R^6$, $R^7$, $R^8$ and $R^9$ may mutually bond at the end to form an alkylene chain, at least one of $R^6$, $R^7$, $R^8$ and $R^9$ represents an alkyloxyethoxyethyl group of the formula (4), and $A^-$ represents a bis(trifluoromethylsulfonyl)imidate ion $[N(SO_2CF_3)_2^-]$, tetrafluoroborate ion $(BF_4^-)$ or hexafluorophosphate ion $(PF_6^-)$].

[5] The quaternary ammonium salt according to [4] wherein at least one of $R^6$, $R^7$, $R^8$ and $R^9$ represents a methyl group.

[6] The quaternary ammonium salt according to [4] wherein any two of $R^6$, $R^7$, $R^8$ and $R^9$ represent a methyl group.

[7] The quaternary ammonium salt according to [1] wherein the quaternary ammonium salt is represented by the following formula (5):

$$\{(R^{10})_k(R^{11})_l(R^5OCH_2CH_2)_m(R^4OCH_2CH_2OCH_2CH_2)_nN\}^+ \cdot A^- \quad (5)$$

[wherein, $R^{10}$ and $R^{11}$ may be mutually the same or different and represent an alkyl group having 1 to 4 carbon atoms, may mutually bond at the end to form an alkylene chain, $R^4$ and $R^5$ may be mutually the same or different and represent a methyl group or ethyl group, k and l represent an integer of 0 to 2, m and n represent an integer of 1 to 3, the sum of k and l is 2 or less, the sum of k, l, m and n is 4, and $A^-$ represents a bis(trifluoromethylsulfonyl)imidate ion $[N(SO_2CF_3)_2^-]$, tetrafluoroborate ion $(BF_4^-)$ or hexafluorophosphate ion $(PF_6^-)$].

[8] The quaternary ammonium salt according to [7] wherein either $R^{10}$ or $R^{11}$ represents a methyl group, and the sum of k and l is 1 or 2.

[9] The quaternary ammonium salt according to [7] wherein $R^{10}$ and $R^{11}$ represent a methyl group, and k and l represent 1.

[10] An electrolyte comprising the quaternary ammonium salt according to [1], [4] or [7].

MODES FOR CARRYING OUT THE INVENTION

The present invention will be illustrated in detail below.

The quaternary ammonium salt of the present invention is a quaternary ammonium salt of the above-mentioned formula (1).

In the formula (1), $R^1$, $R^2$ and $R^3$ may be mutually the same or different and represent an alkyl group having 1 to 4 carbon atoms or an alkyloxyethyl group of the formula (2):

$$R^5OCH_2CH_2— \quad (2),$$

$R^5$ in the formula (2) being a methyl group or ethyl group. $R^4$ in the formula (1) represents a methyl group or ethyl group.

Any two of $R^1$, $R^2$ and $R^3$ may mutually bond at the end to form an alkylene chain.

a, b and c represent an integer of 0 to 3, d represents an integer of 1 to 4, the sum of a, b and c is 3 or less, and the sum of a, b, c and d is 4.

Preferably used are N-methyl bodies, N,N-dimethyl bodies and N,N,N-trimethyl bodies in which at least one of $R^1$, $R^2$ and $R^3$ represents a methyl group, and the sum of a, b and c is 1 to 3.

More preferably used are N,N-dimethyl bodies and N,N,N-trimethyl bodies in which any two of $R^1$, $R^2$ and $R^3$ represent a methyl group, and the sum of a, b and c is 1 to 3.

$A^-$ represents a bis(trifluoromethylsulfonyl)imidate ion $[N(SO_2CF_3)_2^-]$, tetrafluoroborate ion $(BF_4^-)$ or hexafluorophosphate ion $(PF_6^-)$.

Here, examples of the alkyl group having 1 to 4 carbon atoms include a methyl group, ethyl group, propyl group, isopropyl group, butyl group, isobutyl group and the like.

Examples of the alkylene chain formed by mutual bonding of any two of $R^1$, $R^2$ and $R^3$ at the end include a tetramethylene group, pentamethylene group and the like.

When the alkylene chain formed is a tetramethylene group, a pyrrolidine ring is formed between this tetramethylene group and a nitrogen atom constituting a cation of a quaternary ammonium salt.

When the alkylene chain formed is a pentamethylene group, a piperidine ring is formed between this pentamethylene group and a nitrogen atom constituting a cation of a quaternary ammonium salt.

The quaternary ammonium salt of the formula (1) of the present invention can be produced by various methods, and preferable production methods include the following method and the like.

For example, there are mentioned a production method in which a quaternary ammonium halide of the formula (6)

$$\{(R^1)_a(R^2)_b(R^3)_c(R^4OCH_2CH_2OCH_2CH_2)_d N\}^+ \cdot X^- \quad (6)$$

(wherein, $R^1$ to $R^4$, a, b, c and d have the same meanings as described above, and X represents a halogen atom) is reacted with a compound of the formula (7):

$$MA \quad (7)$$

(wherein, M represents a hydrogen atom or alkali metal, and A has the same meaning as described above), to allow a halogen ion of the quaternary ammonium halide (6) to be ion-exchanged with a bis(trifluoromethylsulfonyl)imidate ion $[N(SO_2CF_3)_2^-]$, tetrafluoroborate ion $(BF_4^-)$ or hexafluorophosphate ion $(PF_6^-)$; and other methods.

As the halogen ion of the quaternary ammonium halide (6), for example, a chlorine ion, bromine ion, iodine ion and the like are mentioned.

Examples of the compound (7) include bis(trifluoromethylsulfonyl)imidic acid $[HN(SO_2CF_3)_2]$, tetrafluoroboric acid $(HBF_4)$, hexafluorophosphoric acid $(HPF_6)$, alkali metal salts thereof (for example, lithium salt, sodium salt, potassium salt and the like), and the like.

Ion exchange is carried out usually according to the following method.

The quaternary ammonium halide (6) and the compound (7) are mixed in water, an organic solvent showing low solubility in water (for example, ethyl acetate, methylene chloride and the like) is mixed with the resulted aqueous solution, then, an aqueous layer and an organic layer are separated, thus, a solution of a quaternary ammonium salt of the present invention can be obtained as the organic layer. The quaternary ammonium salt of the present invention can be obtained as a residue by washing the resulted organic layer with water if necessary, then, removing the organic solvent by distillation.

Here, the amount of the compound (7) used is usually 1.0 mol to 1.5 mol, preferably 1.0 mol to 1.1 mol based on 1 mol of the quaternary ammonium halide (6). The amount of water used in mixing the quaternary ammonium halide (6) and the compound (7) is usually 1 to 10 parts by weight, preferably 1 to 4 parts by weight based on 1 part by weight of the quaternary ammonium halide (6). Mixing of the quaternary ammonium halide (6) and the compound (7) in water is carried out at usually 10 to 60° C., preferably at 10 to 30 for usually 1 to 24 hours, preferably 1 to 4 hours.

The amount of an organic solvent used is usually 1 to 10 parts by weight, preferably 1 to 4 parts by weight based on 1 part by weight of the quaternary ammonium halide (6).

The quaternary ammonium halide (6) can be produced by reacting a tertiary amine of the formula (8):

$$(R^{12})_e(R^{13})_f(R^{14})_g N \quad (8)$$

[wherein, $R^{12}$, $R^{13}$ and $R^{14}$ may be mutually the same or different and represent an alkyl group having 1 to 4 carbon atoms, an alkyloxyethyl group of the formula (2):

$$R^5OCH_2CH_2— \quad (2)$$

(wherein, $R^5$ has the same meaning as described above), or an alkyloxyethoxyethyl group of the formula (4):

$$R^4OCH_2CH_2OCH_2CH_2— \quad (4)$$

(wherein, $R^4$ has the same meaning as described above), and any two of $R^{12}$, $R^{13}$ and $R^{14}$ may bond at the end to form an alkylene chain, $R^4$ and $R^5$ have the same meanings as described above, e, f and g represent an integer of 0 to 3, and the sum of e, f and g is 3] with a halogeno-ether compound of the formula (9):

$$R^4OCH_2CH_2OCH_2CH_2—X \quad (9)$$

(wherein, $R^4$ and X have the same meanings as described above).

For example, the quaternary ammonium halide (6) can be obtained by mixing the tertiary amine (8), halogeno-ether-compound (9) and solvent (alcohols such as methanol, ethanol, isopropanol and the like, acetonitrile, ethyl acetate, tetrahydrofuran, dimethylformamide and the like) and stirring the mixture.

The amount of the halogeno-ether compound (9) used is usually 0.5 to 2.0 mol, preferably 0.8 to 1.2 mol based on 1 mol of the tertiary amine (8). The amount of the solvent used is usually 1 to 10 parts by weight, preferably 1 to 4 parts by weight based on 1 part by weight of the tertiary amine (8).

The temperature and time for mixing and stirring are appropriately selected depending on the kind of the solvent used in the reaction, and the reaction temperature is usually 20° C. or more, preferably 60 to 120° C., and the reaction time is usually 4 hours or more, preferably 4 to 24 hours, more preferably 4 to 12 hours.

After thus obtaining a reaction mixture containing the quaternary ammonium halide (6), the resulted reaction mixture is concentrated and dried to obtain a residue containing the quaternary ammonium halide (6) as a main component. This residue can be used as it is in an ion exchange reaction, however, if necessary, the residue is mixed with an organic solvent (for example, ethyl ether, ethyl acetate, methyl ethyl ketone, methyl isobutyl ketone and the like), unreacted raw materials and the like contained in the residue are dissolved in an organic solvent, then, filtrated, thus, a quaternary ammonium halide (6) of high purity can be obtained as a filtration residue.

The quaternary ammonium salt of the present invention is preferably a quaternary ammonium salt of the above-mentioned formula (3).

In the formula (3), $R^6$, $R^7$ $R^8$ and $R^9$ may be mutually the same or different and represent an alkyl group having 1 to 4 carbon atoms or an alkyloxyethoxyethyl group of the formula (4):

$$R^4OCH_2CH_2OCH_2CH_2— \quad (4)$$

(wherein, $R^4$ represents a methyl group or ethyl group), and any two of $R^6$, $R^7$, $R^8$ and $R^9$ may mutually bond at the end to form an alkylene chain. Here, at least one of $R^6$, $R^7$, $R^8$ and $R^9$ represents an alkyloxyethoxyethyl group of the formula (4).

It is preferable that at least one of $R^6$, $R^7$, $R^8$ and $R^9$ represents a methyl group.

It is more preferable that any two of $R^6$, $R^7$, $R^8$ and $R^9$ represent a methyl group.

$A^-$ represents a bis(trifluoromethylsulfonyl)imidate ion $[N(SO_2CF_3)_2^-]$, tetrafluoroborate ion $(BF_4^-)$ or hexafluorophosphate ion $(PF_6^-)$].

Here, examples of the alkyl group having 1 to 4 carbon atoms include a methyl group, ethyl group, propyl group, isopropyl group, butyl group, isobutyl group and the like.

Examples of the alkylene chain formed by mutual bonding of any two of $R^6$, $R^7$, $R^8$ and $R^9$ at the end include a tetramethylene group, pentamethylene group and the like.

When the alkylene chain formed is a tetramethylene group, a pyrrolidine ring is formed between this tetramethylene group and a nitrogen atom constituting a cation of a quaternary ammonium salt.

When the alkylene chain formed is a pentamethylene group, a piperidine ring is formed between this pentamethylene group and a nitrogen atom constituting a cation of a quaternary ammonium salt.

Examples of the quaternary ammonium salt of the formula (3) include N,N-dimethyl-N-ethyl-N-methoxyethoxyethylammonium bis(trifluoromethylsulfonyl)imidate of the formula:

$$\{(CH_3)_2(CH_3CH_2)(CH_3OCH_2CH_2OCH_2CH_2)N\}^+.N(SO_2CF_3)_2^-$$

N,N,N-trimethyl-N-methoxyethoxyethylammonium bis(trifluoromethylsulfonyl)imidate of the formula:

$$\{(CH_3)_3(CH_3OCH_2CH_2OCH_2CH_2)N\}^+.N(SO_2CF_3)_2^-$$

N,N-diethyl-N-methyl-N-methoxyethoxyethylammonium bis(trifluoromethylsulfonyl)imidate of the formula:

$$\{(CH_3)(CH_3CH_2)_2(CH_3OCH_2CH_2OCH_2CH_2)N\}^+.N(SO_2CF_3)_2^-$$

N,N,N-triethyl-N-methoxyethoxyethylammonium bis(trifluoromethylsulfonyl)imidate of the formula:

$$\{(CH_3CH_2)_3(CH_3OCH_2CH_2OCH_2CH_2)N\}^+.N(SO_2CF_3)_2^-$$

N,N-dimethyl-N-ethyl-N-ethoxyethoxyethylammonium bis(trifluoromethylsulfonyl)imidate of the formula:

$$\{(CH_3)_2(CH_3CH_2)(CH_3CH_2OCH_2CH_2OCH_2CH_2)N\}^+.N(SO_2CF_3)_2^-$$

N-methyl-N-methoxyethoxyethylpyrrolidinium bis(trifluoromethylsulfonyl)imidate of the formula:

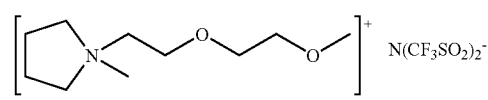

N,N-dimethyl-N,N-di(ethoxyethoxyethyl)ammonium bis(trifluoromethylsulfonyl)imidate of the formula:

$$\{(CH_3)_2(CH_3CH_2OCH_2CH_2OCH_2CH_2)(CH_3CH_2OCH_2CH_2OCH_2CH_2)N\}^+.N(SO_2CF_3)_2^-$$

N,N-dimethyl-N-ethoxyethoxyethyl-N-methoxyethoxyethylammonium bis(trifluoromethylsulfonyl)imidate of the formula:

$$\{(CH_3)_2(CH_3OCH_2CH_2OCH_2CH_2)(CH_3CH_2OCH_2CH_2OCH_2CH_2)N\}^+.N(SO_2CF_3)_2^-$$

N,N-dimethyl-N-ethyl-N-methoxyethoxyethylammonium tetrafluoroborate of the formula:

$$\{(CH_3)_2(CH_3CH_2)(CH_3OCH_2CH_2OCH_2CH_2)N\}^+.BF_4^-$$

N,N,N-trimethyl-N-methoxyethoxyethylammonium tetrafluoroborate of the formula:

$$\{(CH_3)_3(CH_3OCH_2CH_2OCH_2CH_2)N\}^+.BF_4^-$$

N,N-diethyl-N-methyl-N-methoxyethoxyethylammonium tetrafluoroborate of the formula:

$$\{(CH_3)(CH_3CH_2)_2(CH_3OCH_2CH_2OCH_2CH_2)N\}^+.BF_4^-$$

N,N,N-triethyl-N-methoxyethoxyethylammonium tetrafluoroborate of the formula:

$$\{(CH_3CH_2)_3(CH_3OCH_2CH_2OCH_2CH_2)N\}^+.BF_4^-$$

N,N-dimethyl-N-ethyl-N-ethoxyethoxyethylammonium tetrafluoroborate of the formula:

$$\{(CH_3)_2(CH_3CH_2)(CH_3CH_2OCH_2CH_2OCH_2CH_2)N\}^+.BF_4^-$$

N-methyl-N-methoxyethoxyethylpyrrolidinium tetrafluoroborate of the formula:

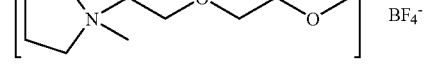

N,N-dimethyl-N,N-di(ethoxyethoxyethyl)ammonium tetrafluoroborate of the formula:

N,N-dimethyl-N-ethoxyethoxyethyl-N-methoxyethoxyethylammonium tetrafluoroborate of the formula:

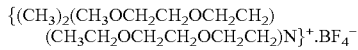

and the like.

OF them,

N,N-dimethyl-N-ethyl-N-methoxyethoxyethylammonium bis(trifluoromethylsulfonyl)imidate

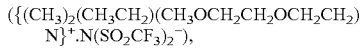

N,N,N-trimethyl-N-methoxyethoxyethylammonium bis(trifluoromethylsulfonyl)imidate

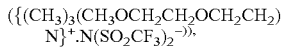

N,N-dimethyl-N-ethyl-N-ethoxyethoxyethylammonium bis(trifluoromethylsulfonyl)imidate

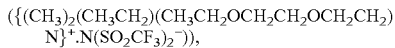

N-methyl-N-methoxyethoxyethylpyrrolidinium bis(trifluoromethylsulfonyl)imidate (following formula):

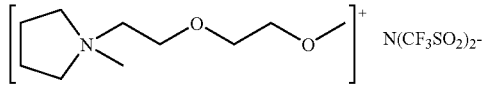

N,N-dimethyl-N-ethyl-N-methoxyethoxyethylammonium tetrafluoroborate

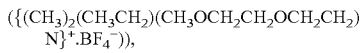

N,N,N-trimethyl-N-methoxyethoxyethylammonium tetrafluoroborate $(\{(CH_3)_3(CH_3OCH_2CH_2OCH_2CH_2)N\}^+$ $.BF_4^-))$, N,N-diethyl-N-methyl-N-methoxyethoxyethylammonium tetrafluoroborate

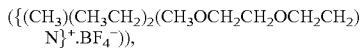

N,N-dimethyl-N-ethyl-N-ethoxyethoxyethylammonium tetrafluoroborate

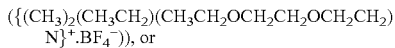, or

N-methyl-N-methoxyethoxyethylpyrrolidinium tetrafluoroborate (following formula):

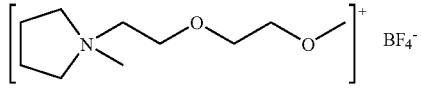

is preferably used.

The quaternary ammonium salt of the formula (3) of the present invention can be produced by various methods. Mentioned as preferable production methods are a production method in which a quaternary ammonium halide of the formula (10)

 (10)

(wherein, $R^6$, $R^7$, $R^8$ and $R^9$ have the same meanings as described above, and X represents a halogen atom), is reacted with a compound of the formula (7):

MA (7)

(wherein, M and A have the same meanings as described above), to allow a halogen ion of the quaternary ammonium halide (10) to be ion-exchanged with a bis(trifluoromethylsulfonyl)imidate ion $[N(SO_2CF_3)_2^-]$, tetrafluoroborate ion $(BF_4^-)$ or hexafluorophosphate ion $(PF_6^-)$; and other methods.

As the halogen ion of the quaternary ammonium halide (10), for example, a chlorine ion, bromine ion, iodine ion and the like are mentioned.

Examples of the compound (7) include bis(trifluoromethylsulfonyl)imidic acid $[HN(SO_2CF_3)_2]$, tetrafluoroboric acid $(HBF_4)$, hexafluorophosphoric acid $(HPF_6)$, alkali metal salts thereof (for example, lithium salt, sodium salt, potassium salt and the like), and the like.

Ion exchange is carried out usually according to the following method.

The quaternary ammonium halide (10) and the compound (7) are mixed in water, an organic solvent showing low solubility in water (for example, ethyl acetate, methylene chloride and the like) is mixed with the resulted aqueous solution, then, an aqueous layer and an organic layer are separated, thus, a solution of a quaternary ammonium salt of the present invention can be obtained as the organic layer. The quaternary ammonium salt of the present invention can be obtained as a residue by washing the resulted organic layer with water if necessary, then, removing the organic solvent by distillation.

Here, the amount of the compound (7) used is usually 1.0 mol to 1.5 mol, preferably 1.0 mol to 1.1 mol based on 1 mol of the quaternary ammonium halide (10). The amount of water used in mixing the quaternary ammonium halide (10) and the compound (7) is usually 1 to 10 parts by weight, preferably 1 to 4 parts by weight based on 1 part by weight of the quaternary ammonium halide (10). Mixing of the quaternary ammonium halide (10) and the compound (7) in water is carried out at usually 10 to 60° C., preferably at 10 to 30° C. for usually 1 to 24 hours, preferably 1 to 4 hours.

The amount of an organic solvent used is usually 1 to 10 parts by weight, preferably 1 to 4 parts by weight based on 1 part by weight of the quaternary ammonium halide (10).

The quaternary ammonium halide (10) can be produced by reacting a tertiary amine of the formula (11):

 (11)

(wherein, $R^6$, $R^7$ and $R^8$ have the same meanings as described above).

with a halogeno-compound of the formula (12):

 (12)

(wherein, $R^9$ and X have the same meanings as described above).

For example, the quaternary ammonium halide (10) can be obtained by mixing the tertiary amine (11), halogeno-compound (12) and solvent (alcohols such as methanol, ethanol, isopropanol and the like, acetonitrile, ethyl acetate, tetrahydrofuran, dimethylformamide and the like) and stirring the mixture.

The amount of the halogeno-compound (12) used is usually 0.5 to 2.0 mol, preferably 0.8 to 1.2 mol based on 1 mol of the tertiary amine (11). The amount of the solvent used is usually 1 to 10 parts by weight, preferably 1 to 4 parts by weight based on 1 part by weight of the tertiary amine (11).

The temperature and time for mixing and stirring are appropriately selected depending on the kind of the solvent used in the reaction, and the reaction temperature is usually 20° C. or more, preferably 60 to 120° C., and the reaction time is usually 4 hours or more, preferably 4 to 24 hours, more preferably 4 to 12 hours.

After thus obtaining a reaction mixture containing the quaternary ammonium halide (10), the resulted reaction mixture is concentrated and dried to obtain a residue containing the quaternary ammonium halide (10) as a main component. This residue can be used as it is in an ion exchange reaction, however, if necessary, the residue is mixed with an organic solvent (for example, ethyl ether, ethyl acetate, methyl ethyl ketone, methyl isobutyl ketone and the like), unreacted raw materials and the like contained in the residue are dissolved in an organic solvent, then, filtrated, thus, a quaternary ammonium halide (10) of high purity can be obtained as a filtration residue.

The quaternary ammonium salt of the present invention is preferably a quaternary ammonium salt of the above-mentioned formula (5).

In the formula (5), $R^{10}$ and $R^{11}$ may be mutually the same or different and represent an alkyl group having 1 to 4 carbon atoms, and may mutually bond at the end to form an alkylene chain.

k and l represent an integer of 0 to 2, m and n represent an integer of 1 to 3, the sum of k and l is 2 or less, and the sum of k, l, m and n is 4.

It is preferable that either $R^{10}$ or $R^{11}$ represents a methyl group, and the sum of k and l is 1 or 2.

It is more preferable that $R^{10}$ and $R^{11}$ represent a methyl group, and k and l represent 1.

$R^4$ and $R^5$ may be mutually the same or different and represent a methyl group or ethyl group.

$A^-$ represents a bis(trifluoromethylsulfonyl)imidate ion $[N(SO_2CF_3)_2^-]$, tetrafluoroborate ion ($BF_4^-$) or hexafluorophosphate ion ($PF_6^-$).

Here, examples of the alkyl group having 1 to 4 carbon atoms include a methyl group, ethyl group, propyl group, isopropyl group, butyl group, isobutyl group and the like.

Examples of the alkylene chain formed by mutual bonding of any two of $R^{10}$ and $R^{11}$ at the end include a tetramethylene group, pentamethylene group and the like.

When the alkylene chain formed is a tetramethylene group, a pyrrolidine ring is formed between this tetramethylene group and a nitrogen atom constituting a cation of a quaternary ammonium salt.

When the alkylene chain formed is a pentamethylene group, a piperidine ring is formed between this pentamethylene group and a nitrogen atom constituting a cation of a quaternary ammonium salt.

Examples of the quaternary ammonium salt of the formula (5) include, in which either $R^{10}$ or $R^{11}$ represents a methyl group and the sum of k and l is 1 or 2, N,N-dimethyl-N-ethoxyethyl-N-methoxyethoxyethylammonium bis(trifluoromethylsulfonyl)imidate of the formula:

$$\{(CH_3)_2(CH_3CH_2OCH_2CH_2)(CH_3OCH_2CH_2OCH_2CH_2)N\}^+ \cdot N(SO_2CF_3)_2^-$$

N-ethyl-N-methoxyethoxyethyl-N-methoxyethyl-N-methylammonium bis(trifluoromethylsulfonyl)imidate of the formula:

$$\{(CH_3)(CH_3CH_2)(CH_3OCH_2CH_2)(CH_3OCH_2CH_2OCH_2CH_2)N\}^+ \cdot N(SO_2CF_3)_2^-$$

N,N-dimethyl-N-methoxyethoxyethyl-N-methoxyethylammonium bis(trifluoromethylsulfonyl)imidate of the formula:

$$\{(CH_3)_2(CH_3OCH_2CH_2)(CH_3OCH_2CH_2OCH_2CH_2)N\}^+ \cdot N(SO_2CF_3)_2^-$$

N-methoxyethoxyethyl-N-methoxyethylpyrrolidinium bis(trifluoromethylsulfonyl)imidate of the formula:

N,N-di(ethoxyethyl)-N-methoxyethoxyethyl-N-methylammonium bis(trifluoromethylsulfonyl)imidate of the formula:

$$\{(CH_3)(CH_3CH_2OCH_2CH_2)(CH_3CH_2OCH_2CH_2)(CH_3OCH_2CH_2OCH_2CH_2)N\}^+ \cdot N(SO_2CF_3)_2^-$$

N,N-di(ethoxyethyl)-N-ethoxyethoxyethyl-N-methylammonium bis(trifluoromethylsulfonyl)imidate of the formula:

$$\{(CH_3)(CH_3CH_2OCH_2CH_2)(CH_3CH_2OCH_2CH_2)(CH_3CH_2OCH_2CH_2OCH_2CH_2)N\}^+ \cdot N(SO_2CF_3)_2^-$$

N,N-dimethyl-N-ethoxyethyl-N-methoxyethoxyethylammonium tetrafluoroborate of the formula:

$$\{(CH_3)_2(CH_3CH_2OCH_2CH_2)(CH_3OCH_2CH_2OCH_2CH_2)N\}^+ \cdot BF_4^-$$

N-ethyl-N-methoxyethoxyethyl-N-methoxyethyl-N-methylammonium tetrafluoroborate of the formula:

$$\{(CH_3)(CH_3CH_2)(CH_3OCH_2CH_2)(CH_3OCH_2CH_2OCH_2CH_2)N\}^+ \cdot BF_4^-$$

N,N-dimethyl-N-methoxyethoxyethyl-N-methoxyethylammonium tetrafluoroborate of the formula:

$$\{(CH_3)_2(CH_3OCH_2CH_2)(CH_3OCH_2CH_2OCH_2CH_2)N\}^+ \cdot BF_4^-$$

N-methoxyethoxyethyl-N-methoxyethylpyrrolidinium tetrafluoroborate of the formula:

N,N-di(ethoxyethyl)-N-methoxyethoxyethyl-N-methylammonium tetrafluoroborate of the formula:

$$\{(CH_3)(CH_3CH_2OCH_2CH_2)(CH_3CH_2OCH_2CH_2)(CH_3OCH_2CH_2OCH_2CH_2)N\}^+ \cdot BF_4^-$$

N,N-di(ethoxyethyl)-N-ethoxyethoxyethyl-N-methylammonium tetrafluoroborate of the formula:

$$\{(CH_3)(CH_3CH_2OCH_2CH_2)(CH_3CH_2OCH_2CH_2)(CH_3CH_2OCH_2CH_2OCH_2CH_2)N\}^+ BF_4^-$$

and the like.

Of them, in which either $R^{10}$ and $R^{11}$ represent a methyl group and the sum of k and l is 1 or 2, N,N-dimethyl-N-ethoxyethyl-N-methoxyethoxyethylammonium bis(trifluoromethylsulfonyl)imidate of the formula:

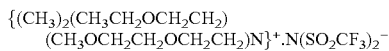
{(CH$_3$)$_2$(CH$_3$CH$_2$OCH$_2$CH$_2$)
(CH$_3$OCH$_2$CH$_2$OCH$_2$CH$_2$)N}$^+$·N(SO$_2$CF$_3$)$_2^-$ N,N-dimethyl-N-methoxyethoxyethyl-N-methoxyethylammonium bis(trifluoromethylsulfonyl)imidate of the formula:

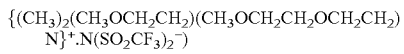
{(CH$_3$)$_2$(CH$_3$OCH$_2$CH$_2$)(CH$_3$OCH$_2$CH$_2$OCH$_2$CH$_2$)N}$^+$·N(SO$_2$CF$_3$)$_2^-$)

are preferably used.

The quaternary ammonium salt of the formula (5) of the present invention can be produced by various methods. Mentioned as preferable production methods are a production method in which a quaternary ammonium halide of the formula (13)

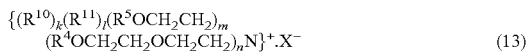
{(R$^{10}$)$_k$(R$^{11}$)$_l$(R$^5$OCH$_2$CH$_2$)$_m$(R$^4$OCH$_2$CH$_2$OCH$_2$CH$_2$)$_n$N}$^+$·X$^-$  (13)

(wherein, $R^4$, $R^5$, $R^{10}$, $R^{11}$, k, l, m and n have the same meanings as described above, and X represents a halogen atom) is reacted with a compound of the formula (7):

MA  (7)

(wherein, M and A have the same meanings as described above) to allow a halogen ion of the quaternary ammonium halide (13) to be ion-exchanged with a bis(trifluoromethylsulfonyl)imidate ion [N(SO$_2$CF$_3$)$_2^-$], tetrafluoroborate ion (BF$_4^-$) or hexafluorophosphate ion (PF$_6^-$); and other methods.

As the halogen ion of the quaternary ammonium halide (13), for example, a chlorine ion, bromine ion, iodine ion and the like are mentioned.

Examples of the compound (7) include bis(trifluoromethylsulfonyl)imidic acid [HN(SO$_2$CF$_3$)$_2$], tetrafluoroboric acid (HBF$_4$), hexafluorophosphoric acid (HPF$_6$), alkali metal salts thereof (for example, lithium salt, sodium salt, potassium salt and the like), and the like.

Ion exchange is carried out usually according to the following method.

The quaternary ammonium halide (13) and the compound (7) are mixed in water, an organic solvent showing low solubility in water (for example, ethyl acetate, methylene chloride and the like) is mixed with the resulted aqueous solution, then, an aqueous layer and an organic layer are separated, thus, a solution of a quaternary ammonium salt of the present invention can be obtained as the organic layer. The quaternary ammonium salt of the present invention can be obtained as a residue by washing the resulted organic layer with water if necessary, then, removing the organic solvent by distillation.

Here, the amount of the compound (7) used is usually 1.0 mol to 1.5 mol, preferably 1.0 mol to 1.1 mol based on 1 mol of the quaternary ammonium halide (13). The amount of water used in mixing the quaternary ammonium halide (13) and the compound (7) is usually 1 to 10 parts by weight, preferably 1 to 4 parts by weight based on 1 part by weight of the quaternary ammonium halide (13). Mixing of the quaternary ammonium halide (13) and the compound (7) in water is carried out at usually 10 to 60° C., preferably at 10 to 30° C. for usually 1 to 24 hours, preferably 1 to 4 hours.

The amount of an organic solvent used is usually 1 to 10 parts by weight, preferably 1 to 4 parts by weight based on 1 part by weight of the quaternary ammonium halide (13).

The quaternary ammonium halide (13) can be produced by reacting a tertiary amine of the formula (14):

N(R$^{15}$)$_p$(R$^{16}$)$_q$(CH$_2$CH$_2$OR$^5$)$_r$  (14)

[wherein, $R^{15}$ and $R^{16}$ may be mutually the same or different and represent an alkyl group having 1 to 4 carbon atoms, or an alkyloxyethoxyethyl group of the formula (4):

R$^4$OCH$_2$CH$_2$OCH$_2$CH$_2$—  (4)

(wherein, $R^4$ has the same meaning as described above), and $R^{15}$ and $R^{16}$ may bond at the end to form an alkylene chain. $R^5$ has the same meaning as described above p and q represent an integer of 0 to 2, and r represents an integer of 1 to 3. Here, the sum of p and q is 2 or less, and the sum of p, q and r is 3.]

with a halogeno-ether-compound of the formula (9):

R$^4$OCH$_2$CH$_2$OCH$_2$CH$_2$—X  (9)

(wherein, $R^4$ and X have the same meanings as described above).

For example, the quaternary ammonium halide (13) can be obtained by mixing the tertiary amine (14), halogeno-compound (9) and solvent (alcohols such as methanol, ethanol, isopropanol and the like, acetonitrile, ethyl acetate, tetrahydrofuran, dimethylformamide and the like) and stirring the mixture.

The amount of the halogeno-compound (9) used is usually 0.5 to 2.0 mol, preferably 0.8 to 1.2 mol based on 1 mol of the tertiary amine (14). The amount of the solvent used is usually 1 to 10 parts by weight, preferably 1 to 4 parts by weight based on 1 part by weight of the tertiary amine (14).

The temperature and time for mixing and stirring are appropriately selected depending on the kind of the solvent used in the reaction, and the reaction temperature is usually 20° C. or more, preferably 60 to 120° C., and the reaction time is usually 4 hours or more, preferably 4 to 24 hours, more preferably 4 to 12 hours.

After thus obtaining a reaction mixture containing the quaternary ammonium halide (13), the resulted reaction mixture is concentrated and dried to obtain a residue containing the quaternary ammonium halide (13) as a main component. This residue can be used as it is in an ion exchange reaction, however, if necessary, the residue is mixed with an organic solvent (for example, ethyl ether, ethyl acetate, methyl ethyl ketone, methyl isobutyl ketone and the like), unreacted raw materials and the like contained in the residue are dissolved in an organic solvent, then, filtrated, thus, a quaternary ammonium halide (13) of high purity can be obtained as a filtration residue.

The tertiary amine (14) can be produced by various methods. Mentioned as preferable production methods are a production method in which a primary amine or secondary amine of the formula (15)

NH(R$^{17}$)$_s$(CH$_2$CH$_2$OR$^5$)$_t$  (15)

[wherein, $R^{17}$ represents a hydrogen atom, alkyl group having 1 to 4 carbon atoms or an alkyloxyethoxyethyl group of the formula (4):

R$^4$OCH$_2$CH$_2$OCH$_2$CH$_2$—  (4)

(wherein, $R^4$ has the same meaning as described above), and $R^5$ has the same meaning as described above. s represents an integer of 0 to 1, and r represents an integer of 1 to 2. Here, the sum of s and t is 2.]

is reacted with an aldehyde of the formula (16):

R$^{18}$CHO  (16)

(wherein, $R^{18}$ represents a hydrogen atom or alkyl group having 1 to 3 carbon atoms) in an autoclave in the presence of a catalyst under hydrogen pressurization condition; and other methods.

For example, the primary or secondary amine (15), solvent (alcohols such as methanol, ethanol, isopropanol and the like, water and the like), metal catalyst (for example, sponge Ni, palladium carbon, and the like) and aldehyde (16) are mixed and charged in an autoclave, and reacted while feeding hydrogen. The aldehyde (16) may be, if necessary, introduced into the autoclave under pressure after heating the autoclave. After thus obtaining a reaction mixture containing the tertiary amine (14), the resulted reaction mixture can be distilled to obtain the tertiary amine (14).

The amount of the solvent used is usually 0.2 to 10 parts by weight, preferably 0.2 to 2 parts by weight based on 1 part by weight of the primary or secondary amine (15). The amount of the metal catalyst used is usually 0.01 to 0.3 parts by weight, preferably 0.05 to 0.15 parts by weight based on 1 part of the primary or secondary amine (15). The amount of the aldehyde (16) used is, when the amine (15) is a primary amine, usually 2.0 to 4.0 mol, preferably 2.0 to 2.2 mol based on 1 mol of the primary amine, and when the amine (15) is a secondary amine, usually 1.0 to 2.0 mol, preferably 1.0 to 1.2 mol based on 1 mol of the secondary amine. The temperature is usually 40° C. or more, preferably 60 to 120° C., and the hydrogen pressure is usually 1 MPa or more, preferably 3 to 7 MPa. The reaction time is usually 4 to 12 hours.

EXAMPLES

The present invention will be illustrated more specifically by the following examples, but it is needless to say that these examples do not limit the scope of the invention.

Example 1

A mixture of 5.12 g (0.070 mol) of dimethylethylamine, 14.2 g (0.070 mol) of 1-bromo-2-(methoxyethoxy)ethane and 10.2 g of acetonitrile was stirred at 80° C. for 24 hours for reaction thereof. After completion of the reaction, the resulted reaction mixture was concentrated, and the residue was dried under reduced pressure to obtain 18.4 g (0.070 mol) of N,N-dimethyl-N-ethyl-N-methoxyethoxyethylammonium bromide.

To 18.4 g (0.070 mol) of N,N-dimethyl-N-ethyl-N-methoxyethoxyethylammonium bromide obtained above was added 36.8 g of water and 0.2 g of activated carbon and stirred at room temperature for 1 hour, and filtrated. Into the filtrate was mixed 20.3 g (0.071 mol) of lithium=bis(trifluoromethylsulfonyl)imidate [$(F_3CSO_2)_2NLi$] and stirred at room temperature for 1 hour, and to the resulted mixture was added 36.8 g of methylene chloride and mixed, then, subjected to separation to obtain 36.8 g of an organic layer which was washed with 36.8 g of water three times. Then, methylene chloride was distilled off from the organic layer to obtain 26.3 g (0.058 mol, yield: 82.2%) of N,N-dimethyl-N-ethyl-N-methoxyethoxyethylammonium bis(trifluoromethylsulfonyl)imidate in the form of oil. The NMR analysis results of the obtained N,N-dimethyl-N-ethyl-N-methoxyethoxyethylammonium bis(trifluoromethylsulfonyl)imidate are shown below.

$^1$H-NMR(CDCl$_3$) δ ppm: 3.90(bm,2H), 3.66-3.64(m,2H), 3.54-3.48(m,6H), 3.34(s,3H), 3.12 (s,6H), 1.39(t,3H)

Example 2 to 9, Comparative Examples 1 to 3

Quaternary ammonium salts were obtained in the same manner as in Example 1 except that tertiary amines, alkoxyethoxyethyl halides, alkoxyethyl halides or alkyl halides, and compounds (7) shown in Table 1 were used as starting raw materials. The NMR analysis results of the obtained quaternary ammonium salts are shown below.

TABLE 1

| | tertiary amine | alkoxy(ethoxy)ethyl halide or alkyl halide | compound (7) |
|---|---|---|---|
| Example 2 | trimethylamine | methoxyethoxyethyl bromide | LiN(SO$_2$CF$_3$)$_2$ |
| Example 3 | diethylmethylamin | methoxyethoxyethyl bromide | LiN(SO$_2$CF$_3$)$_2$ |
| Example 4 | triethylamine | methoxyethoxyethyl bromide | LiN(SO$_2$CF$_3$)$_2$ |
| Example 5 | dimethylethylamine | ethoxyethoxyethyl bromide | LiN(SO$_2$CF$_3$)$_2$ |
| Example 6 | 1-methylpyrrolidine | methoxyethoxyethyl bromide | LiN(SO$_2$CF$_3$)$_2$ |
| Example 7 | dimethylethylamine | methoxyethoxyethyl bromide | NaBF$_4$ |
| Example 8 | trimethylamine | methoxyethoxyethyl bromide | NaBF$_4$ |
| Example 9 | diethylmethylamine | methoxyethoxyethyl bromide | NaBF$_4$ |
| Comparative Example 1 | diethylmethylamine | methoxyethyl chloride | LiN(SO$_2$CF$_3$)$_2$ |
| Comparative Example 2 | diallylmethylamine | hexyl bromide | LiN(SO$_2$CF$_3$)$_2$ |
| Comparative Example 3 | diallylmethylamine | hexyl bromide | NaBF$_4$ |

Quaternary ammonium salt of Example 2: N,N,N-trimethyl-N-methoxyethoxyethylammonium bis(trifluoromethylsulfonyl)imidate $^1$H-NMR(DMSO-d$_6$) δ ppm: 3.83(bm,2H), 3.60-3.57(m,2H), 3.54-3.50(m,2H), 3.48-3.46(m,2H), 3.26(s,3H), 3.10(s,9H)

Quaternary ammonium salt of Example 3: N,N-diethyl-N-methyl-N-methoxyethoxyethylammonium bis(trifluoromethylsulfonyl)imidate $^1$H-NMR(DMSO-d$_6$) δ ppm: 3.80(bm,2H), 3.59-3.56(m,2H), 3.48-3.44(m,4H), 3.35(q,4H), 3.26 (s,3H), 2.96(s,3H), 1.21(t,6H)

Quaternary ammonium salt of Example 4: N,N,N-triethyl-N-methoxyethoxyethylammonium bis(trifluoromethylsulfonyl)imidate $^1$H-NMR(CDCl$_3$) δ ppm: 3.85(bm,2H), 3.65-3.62(m,2H), 3.53-3.51(m,2H), 3.44-3.34(m,11H), 1.32(t,9H)

Quaternary ammonium salt of Example 5: N,N-dimethyl-N-ethyl-N-ethoxyethoxyethylammonium bis(trifluoromethylsulfonyl)imidate $^1$H-NMR(CDCl$_3$) δ ppm: 3.90(bm,2H), 3.66-3.63(m,2H), 3.57-3.55(m,2H), 3.51-3.48(m,6H), 3.12(s,6H), 1.38(t,3H), 1.18(t,3H)

Quaternary ammonium salt of Example 6: N-methyl-N-methoxyethoxyethylpyrrolidinium bis(trifluoromethylsulfonyl)imidate $^1$H-NMR(CDCl$_3$) δ ppm: 3.83(bm,2H), 3.60-3.54(m,4H), 3.51-3.46(m,6H), 3.26(s,3H), 3.02 (s,3H), 2.08(bm,4H)

Quaternary ammonium salt of Example 7: N,N-dimethyl-N-ethyl-N-methoxyethoxyethylammonium tetrafluoroborate $^1$H-NMR(CDCl$_3$) δ ppm: 3.92(bm,2H), 3.66-3.64(m,2H), 3.55-3.50(m,6H), 3.36(s,3H), 3.14 (s,6H), 1.39(t,3H)

Quaternary ammonium salt of Example 8: N,N,N-trimethyl-N-methoxyethoxyethylammonium tetrafluoroborate $^1$H-NMR(CDCl$_3$) δ ppm: 3.93(bm,2H), 3.67-3.63(m,2H), 3.60-3.56(m,2H), 3.55-3.51(m,2H), 3.36(s,3H), 3.23(s,9H)

Quaternary ammonium salt of Example 9: N,N-diethyl-N-methyl-N-methoxyethoxyethylammonium tetrafluoroborate $^1$H-NMR(CDCl$_3$) δ ppm: 3.91(bm,2H), 3.66-3.64(m,2H), 3.54-3.49(m,4H), 3.45(q,4H), 3.36 (s,3H), 3.06(s,3H), 1.36(t,6H)

Quaternary ammonium salt of Comparative Example 1: N,N-diethyl-N-methyl-N-methoxyethoxyethylammonium bis(trifluoromethylsulfonyl)imidate $^1$H-NMR(CDCl$_3$) δ ppm: 3.79(bm,2H), 3.51-3.49(m,2H), 3.44(q,4H), 3.37(s,3H), 3.05(s,3H), 1.36(t,6H)

Quaternary ammonium salt of Comparative Example 2: N,N-diallyl-N-methyl-N-hexylammonium bis(trifluoromethylsulfonyl)imidate $^1$H-NMR(CDCl$_3$) δ ppm: 5.95-5.87(m,2H), 5.76-5.70(m, 4H), 3.85(d,4H), 3.18-3.13(m,2H), 2.96(s,3H), 1.82-1.62(bm,2H), 1.43-1.24(bm,6H), 0.89(bt,3H)

Quaternary ammonium salt of Comparative Example 3: N,N-diallyl-N-methyl-N-hexylammonium tetrafluoroborate $^1$H-NMR(CDCl$_3$) δ ppm: 5.98-5.92(m,2H), 5.78-5.71(m, 4H), 3.94(d,4H), 3.21-3.17(m,2H), 3.03(s,3H), 1.89-1.64(bm,2H), 1.39-1.20(bm,6H), 0.88(bt,3H)

The measurement results of the viscosity and ion conductivity of the quaternary ammonium salts obtained in the above-mentioned examples are summarized in the following tables. The viscosity was measured by using an E-type viscometer (manufactured by Tokyo Keiki K.K.) and the ion conductivity was measured by using a portable electric conductivity meter CM-30S (manufactured by To a DKK K.K.). In the tables, MTE represents a methoxyethyl group, MTETE represents a methoxyethoxyethyl group and ETETE represents an ethoxyethoxyethyl group.

Example 10

A mixture of 133.7 g (1.50 mol) of 2-ethoxyethylamine, 13.4 g of sponge Ni and 22.5 g of methanol was charged in a 1 L autoclave. By introducing 201.3 g (3.09 mol) of a 46% formaldehyde aqueous solution into the autoclave under pressure, The reaction was carried out over 6 hours at 90° C. and 4 MPa of hydrogen. After completion of the reaction, the reaction mixture was filtered, and into the resulted filtrate was dropped 152.1 g (1.50 mol) of 35% hydrochloric acid under ice cool and the mixture was concentrated. The concentrated residue was diluted with 150 g of water, and 210 g of a 30% sodium hydroxide aqueous solution was dropped under ice cool, then, the mixture was extracted with 300 g of methylene chloride. Methylene chloride in the resulted oil layer was distilled off, then, subjected to simple distillation, to obtain 93.3 g (0.80 mol, yield: 53.0%) of N,N-dimethyl-N-ethoxyethylamine.

A mixture of 7.03 g (0.060 mol) of N,N-dimethyl-N-ethoxyethylamine obtained above, 12.2 g (0.060 mol) of 1-bromo-2-(methoxyethoxy)ethane and 14.1 g of acetonitrile was stirred at 80° C. for 24 hours for reaction thereof. After completion of the reaction, the resulted reaction mixture was concentrated, and the residue was dried under reduced pressure to obtain 16.4 g (0.055 mol) of N,N-dimethyl-N-ethoxyethyl-N-methoxyethoxyethylammonium bromide.

16.4 g (0.055 mol) of N,N-dimethyl-N-ethoxyethyl-N-methoxyethoxyethylammonium bromide obtained above, 32.8 g of water and 0.2 g of activated carbon were mixed and stirred at room temperature for 1 hour, and filtrated. With the filtrate was mixed 15.8 g (0.055 mol) of lithium=trifluoromethylsulfonylimidate [(F$_3$CSO$_2$)$_2$NLi] and the mixture was stirred at room temperature for 1 hour, and to the resulted mixture was added 32.8 g of methylene chloride and mixed, then, subjected to separation and the

TABLE 2

| | substituent of the formula (3) | | | | anion of the formula (3) | viscosity (mPa · s) | ion conductivity |
|---|---|---|---|---|---|---|---|
| | R$^6$ | R$^7$ | R$^8$ | R$^9$ | A$^-$ | 25° C. | (25° C.: mS/cm) |
| Comparative Example 1 | CH$_3$ | CH$_3$CH$_2$ | CH$_3$CH$_2$ | MTE | N(SO$_2$CF$_3$)$_2$ | 83.5 | 2.52 |
| Comparative Example 2 | CH$_3$ | CH$_2$=CHCH$_2$ | CH$_2$=CHCH$_2$ | CH$_3$(CH$_2$)$_5$ | N(SO$_2$CF$_3$)$_2$ | 278.0 | 0.58 |
| Example 1 | CH$_3$ | CH$_3$ | CH$_3$CH$_2$ | MTETE | N(SO$_2$CF$_3$)$_2$ | 67.8 | 2.44 |
| Example 2 | CH$_3$ | CH$_3$ | CH$_3$ | MTETE | N(SO$_2$CF$_3$)$_2$ | 73.5 | 2.36 |
| Example 3 | CH$_3$ | CH$_3$CH$_2$ | CH$_3$CH$_2$ | MTETE | N(SO$_2$CF$_3$)$_2$ | 76.5 | 2.17 |
| Example 4 | CH$_3$CH$_2$ | CH$_3$CH$_2$ | CH$_3$CH$_2$ | MTETE | N(SO$_2$CF$_3$)$_2$ | 82.2 | 1.82 |
| Example 5 | CH$_3$ | CH$_3$ | CH$_3$CH$_2$ | ETETE | N(SO$_2$CF$_3$)$_2$ | 65.0 | 2.19 |
| Example 6 | CH$_3$ | MTETE | —(CH$_2$)$_4$— | | N(SO$_2$CF$_3$)$_2$ | 64.3 | 2.66 |

TABLE 3

| | substituent of the formula (3) | | | | anion of the formula (3) | viscosity (mPa · s) |
|---|---|---|---|---|---|---|
| | R$^6$ | R$^7$ | R$^8$ | R$^9$ | A$^-$ | 25° C. |
| Comparative Example 3 | CH$_3$ | CH$_2$=CHCH$_2$ | CH$_2$=CHCH$_2$ | CH$_3$(CH$_2$)$_5$ | BF$_4$ | 2720.0 |
| Example 7 | CH$_3$ | CH$_3$ | CH$_3$CH$_2$ | MTETE | BF$_4$ | 224.6 |
| Example 8 | CH$_3$ | CH$_3$ | CH$_3$ | MTETE | BF$_4$ | 302.1 |
| Example 9 | CH$_3$ | CH$_3$CH$_2$ | CH$_3$CH$_2$ | MTETE | BF$_4$ | 215.1 | resulted organic layer was washed with 32.8 g of water three times. Thereafter, methylene chloride was distilled off from the organic layer, to obtain 26.5 g (0.053 mol, yield: 88.3%) of N,N-dimethyl-N-ethoxyethyl-N-methoxyethoxyethylammonium bis(trifluoromethylsulfonyl)imidate in the form of oil. The NMR analysis results of the obtained N,N-dimethyl-N-ethoxyethyl-N-methoxyethoxyethylammonium bis(trifluoromethylsulfonyl)imidate are shown below.

$^1$H-NMR(CDCl$_3$) δ ppm: 3.94(bm,2H), 3.83(bm,2H), 3.66-3.62(m,6H), 3.54-3.50(m,4H), 3.36(s,3H), 3.22(s,6H), 1.20(t,3H)

Examples 11 to 12

Desired compounds were obtained in the same manner as in Example 1 except that amines and alkoxyethoxyethyl halides shown in Table 4 were used as raw materials. The NMR analysis results of the obtained compounds are shown below.

TABLE 4

| | amine | alkoxyethyloxyethyl halide |
|---|---|---|
| Example 11 | N-ethyl-N-methoxyethylamine | methoxyethoxyethyl bromide |
| Example 12 | N-methoxyethylamine | methoxyethoxyethyl bromide |

Quaternary ammonium salt of Example 11: N-ethyl-N-methoxyethoxyethyl-N-methoxyethyl-N-methylammonium bistrifluoromethylsulfone imidate $^1$H-NMR(CDCl$_3$) δ ppm: 3.90(bm,2H), 3.77(bm,2H), 3.65-3.51(m,10H), 3.37(s,3H), 3.36(s, 3H), 3.12(s,3H), 1.38 (t,3H)

Quaternary ammonium salt of Example 12: N,N-dimethyl-N-methoxyethoxyethyl-N-methoxyethylammonium bistrifluoromethylsulfone imidate $^1$H-NMR(CDCl$_3$) δ ppm: 3.91(bm,2H), 3.79(bm,2H), 3.66-3.61(m,6H), 3.54-3.51(m,2H), 3.37(s,3H), 3.36(s,3H), 3.21(s,6H)

The measurement results of the viscosity and ion conductivity of the quaternary ammonium salts obtained in the above-mentioned examples are summarized in the following table 5. The viscosity was measured by using an E-type viscometer (manufactured by Tokyo Keiki K.K.) and the ion conductivity was measured by using a portable electric conductivity meter CM-30S (manufactured by To a DKK K.K.). In Table 5, MTE represents a methoxyethyl group, ETE represents an ethoxyethyl group and MTETE represents a methoxyethoxyethyl group.

TABLE 5

| | substituent of the formula (17) | | | | viscosity (mPa · s) | ion conductivity (25° C.: |
|---|---|---|---|---|---|---|
| | $R^{19}$ | $R^{20}$ | $R^{21}$ | $R^{22}$ | 25° C. | mS/cm) |
| Comparative Example 1 | CH$_3$ | CH$_3$CH$_2$ | CH$_3$CH$_2$ | MTE | 83.5 | 2.52 |
| Example 10 | CH$_3$ | CH$_3$ | ETE | MTETE | 68.9 | 1.80 |
| Example 11 | CH$_3$ | CH$_3$CH$_2$ | MTE | MTETE | 82.9 | 1.63 |
| Example 12 | CH$_3$ | CH$_3$ | MTE | MTETE | 74.5 | 1.92 |

The formula (17) in Table 5 is a quaternary ammonium salt of the formula (17):

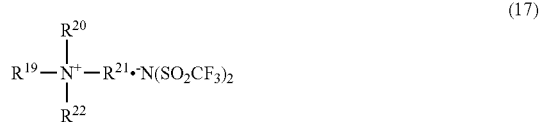

INDUSTRIAL APPLICABILITY

According to the present invention, a quaternary ammonium salt of low viscosity can be provided. The quaternary ammonium salt can be suitably used as a reaction solvent, electrolyte or the like because of its low viscosity.

The invention claimed is:

1. A quaternary ammonium salt of the following formula (3):

wherein, $R^6$, $R^7$, $R^8$ and $R^9$ may be mutually the same or different and represent an alkyl group having 1 to 4 carbon atoms or an alkyloxyethoxyethyl group of the formula (4):

(wherein, $R^4$ represents a methyl group or ethyl group), and at least one of $R^6$, $R^7$, $R^8$ and $R^9$ represents an alkyloxyethoxyethyl group of the formula (4), and A$^-$ represents a bis(trifluoromethylsulfonyl)imidate ion [N(SO$_2$CF$_3$)$_2^-$], tetrafluoroborate ion (BF$_4^-$) or hexafluorophosphate ion (PF$_6^-$) and wherein any two of $R^6$, $R^7$, $R^8$ and $R^9$ represent a methyl group.

2. A quaternary ammonium salt of by the following formula (5):

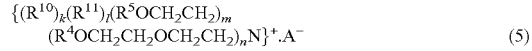

wherein, $R^{10}$ and $R^{11}$ may be mutually the same or different and represent an alkyl group having 1 to 4 carbon atoms, $R^4$ and $R^5$ may be mutually the same or different and represent a methyl group or ethyl group,k and l represent an integer of 0 to 2, m and n represent an integer of 1 to 3, the sum of k and l is 2 or less, the sum of k, l, m and n is 4, and A$^-$ represents a bis(trifluoromethylsulfonyl)imidate ion [N(SO$_2$CF$_3$)$_2^-$], tetrafluoroborate ion (BF$_4^-$) or hexafluorophosphate ion (PF$_6^-$).

3. The quaternary ammonium salt according to claim 2 wherein either $R^{10}$ or $R^{11}$ represents a methyl group, and the sum of k and l is 1 or 2.

4. The quaternary ammonium salt according to claim 2 wherein $R^{10}$ and $R^{11}$ represent a methyl group, and k and l represent 1.

5. An electrolyte comprising the quaternary ammonium salt according to claim 1.

6. An electrolyte comprising the quaternary ammonium salt according to claim 2.

* * * * *